United States Patent
Kindlein et al.

(10) Patent No.: US 7,097,609 B2
(45) Date of Patent: Aug. 29, 2006

(54) AFTER LOADER APPARATUS AS WELL AS A DEVICE FOR EXCHANGING AN AFTER LOADER CARTRIDGE

(75) Inventors: Johann Kindlein, Oberhausen (DE); Frits van Krieken, Dieren (NL); Arie Luite Visscher, Driebergen (NL)

(73) Assignee: Nucletron B.V., Veenendaal (NL)

( * ) Notice: Subject to any disclaimer, the term of this patent is extended or adjusted under 35 U.S.C. 154(b) by 210 days.

(21) Appl. No.: 10/382,511

(22) Filed: Mar. 7, 2003

(65) Prior Publication Data
US 2004/0024284 A1  Feb. 5, 2004

(30) Foreign Application Priority Data
Mar. 27, 2002  (EP) .................................. 02076190

(51) Int. Cl.
  *A61N 5/00*  (2006.01)
  *G21F 5/00*  (2006.01)
(52) U.S. Cl. ..................... 600/7; 250/497.1; 250/507.1
(58) Field of Classification Search ................ 600/1–9; 250/496.1, 497.1, 498.1, 505.1, 506.1, 507.1
  See application file for complete search history.

(56) References Cited
U.S. PATENT DOCUMENTS

| 5,147,282 A | 9/1992 | Kan |
| 5,851,172 A | 12/1998 | Bueche et al. |
| 6,048,300 A | 4/2000 | Thornton et al. |
| 6,137,114 A | 10/2000 | Rohe et al. |
| 6,472,675 B1 * | 10/2002 | White et al. .............. 250/506.1 |

* cited by examiner

*Primary Examiner*—John P. Lacyk
(74) *Attorney, Agent, or Firm*—Birch, Stewart, Kolasch & Birch, LLP

(57) ABSTRACT

The invention relates to an after loader apparatus for treatment of tumours in an animal body comprising a housing with at least one exchangeable radiation source connected to a first end of a transport wire, which wire is connected with its other end to transport means for advancing said transport wire and said radiation source through a guide tube to and from a tumour in said body, where at least the radiation source and the transport wire are mounted in an exchangeable radiation shielded after loader cartridge, which cartridge can be placed in a suitable receptable opening present in said housing.

It is an object of the invention to provide an after loader apparatus wherein in a more safe manner to the environment a cartridge containing a radioactive source can be replaced by another cartridge containing a new radioactive source and according to the invention the after loader apparatus is characterized in that, for exchanging said radiation source after use an exchanging device is present for, in a first step, removing the cartridge with the used radiation source from said receptable opening and, in a second step, inserting a further cartridge containing a new radiation source in said receptable opening.

The invention relates furthermore to a device for exchanging an after loader cartridge in an after loader apparatus according to the invention.

37 Claims, 8 Drawing Sheets

AFTER LOADER APPARATUS AS WELL AS A DEVICE FOR EXCHANGING AN AFTER LOADER CARTRIDGE

The invention relates to an after loader apparatus for treatment of tumours in an animal body comprising a housing with at least one exchangeable radiation source connected to a first end of a transport wire, which wire is connected with its other end to transport means for advancing said transport wire and said radiation source through a guide tube to and from a tumour in said body, where at least the radiation source and the transport wire are mounted in an exchangeable radiation shielded after loader cartridge, which cartridge can be placed in a suitable receptable opening present in said housing.

It is known in the medical field to use after loader devices for the treatment of cancerous tumours using radioactive sources having an intensity greater than that, which can safely be handled. Remote after loaders are devices generally used in the cancer treatment field to accurately advance and retract a flexible wire containing a gamma radiation emitting source over a specified distance for a specific time period. A remote after loader comprises a flexible simulation wire for testing purposes and a flexible wire with the gamma radiation emitting source, specific control and transport mechanisms to operate both types of wires, as well as a radiation shielded housing for the radiation emitting source.

Typically one or more catheters, needles or other closed pathways (hereafter "guide tubes") to the treatment site are positioned in the patient. The guide tubes are then attached to the after loader, which advances the radioactive source at the end of the transport wire, sometimes called a source wire, along the guide tubes according to a predetermined sequence calculated to deliver a therapeutic dose of radiation to the tumour. Many of these prior art devices advance the source-wire by means of a friction drive belt trained about a wheel with the wire sandwiched between the belt and wheel.

The radiation emitting sources presently used are radioactive sources, which sources continuously emit gamma radiation following the principles of natural radioactive decay and which are characterized by the specific half life time of the used radioactive material. Since the sources used in such treatment can constitute a hazard to a technician administering the treatment, after loaders are used for inserting of the radioactive source in the patient with minimum radiation exposure of the technician or with no exposure whatsoever. These after loader devices allow the insertion of the radioactive source in the patient after the technician administering the treatment moves away from the patient or leaves the treatment room. In other words, the radioactive source is loaded into the patient for treatment after the technician leaves the patient, and for that reason such devices are generally referred to as "remote after loading devices".

Normally radioactive sources can be used for these cancer treatments only during a limited time, because of the natural decay of radiation. For this reason the radioactive source has to be exchanged normally sometimes per year. For that purpose in the present after loader apparatus, said radioactive source and said transport wire and in specific embodiments also the transport means are accommodated in an exchangeable cartridge, which cartridge is at least partly radiation shielded can be placed in a suitable receptable opening in the housing of the after loader device. Once the radiation therapy has been administered the transport wire is retracted together with the radioactive source from the patient's body and safely stored inside the cartridge.

In case of replacement, the cartridge together with the used radioactive source is taken out of the receptable opening by hand by a medic or technician administering the therapy to the patient, which used cartridge is then replaced by a similar cartridge containing a new radioactive source together with a transport wire. A new cartridge is placed inside the receptable opening and can then be used for treatment purposes.

An example of an after loading apparatus according to the above introduction is disclosed in U.S. Pat. No. 6,137,114 (K -H. Rohe et al.), wherein the cartridges used contain a High Dose Rate (HDR) or a Pulse Dose Rate (PDR) source. Each cartridge comprises a long-distance radiation source transport container, wherein the HDR or PDR source is stored for replacement and transport purposes. In order to meet the specifications for long-distance radiation source transport containers the whole cartridge construction exhibit enlarged dimensions and weight due to the additional radiation shielding, which shielding is still necessary for an used HDR or PDR source.

Hence, a cartridge as described in U.S. Pat. No 6,137,114 is difficult to be exchanged by technical personnel due to its excessive dimensions and weight.

Another example of such after loading apparatus is disclosed in U.S. Pat. No. 6,048,300 (R. T. Thornton et al.). Especially with the use of so called High Dose Rate sources or Pulse Dose Rate active sources the used transport and exchanged cartridges for such radioactive sources have rather large dimensions and weight, due to the necessary heavy shielding against the radioactive radiation. The manual insertion of such heavy cartridges in the after loader is therefore difficult and not user-friendly.

It is an object of the invention to provide an after loader apparatus wherein in a more safe manner to the environment a cartridge containing a radioactive source can be replaced by another cartridge containing a new radioactive source.

Moreover it is another object of the invention to provide a device for exchanging an after loader cartridge after use, which cartridges can have a simplified construction with reduced dimensions and weight, instead of the long-distance radiation source transport container-cartridge assemblies presently used.

According to the invention the after loader apparatus is characterized in that for exchanging said radiation source after use an exchanging device is present for, in a first step, removing the cartridge with the used radiation source from said receptable opening and, in a second step, inserting a further cartridge containing a new radiation source in said receptable opening.

Thus the exchange of an used cartridge with a new cartridge is performed in a much more controlled manner, thus reducing the risk of accidents or operation errors. Moreover, with such exchanging device according to the invention large and heavy constructed cartridges having a long-distance radiation source transport container are no longer necessary. The cartridges can be constructed in a cheaper, simplified manner with reduced dimensions and weight, whilst maintaining the necessary radiation shielding even when used for HDR or PDR sources. The handling of such cartridges by technical personnel is greatly improved, whilst furthermore a permanent protection against radiation of the personnel is assured.

Such a device can easily be placed against the after loader apparatus containing the used source for automatically replacing said used source with the new source already contained in the exchanging device.

In order to avoid any leakage of radioactive radiation during exchanging the cartridges, said exchanging device comprises connection means, which can cooperate with corresponding connection means present on the housing of the apparatus for coupling said exchanging device to said apparatus. By connecting the exchanging device with the after loader apparatus the exchanging procedure is completely shielded against possible radioactive radiation emitting from the exchanging device and/or apparatus during exchange.

Preferably said corresponding connection means are mounted around said receptable opening.

A fully automation of the exchange of the cartridges is obtained according to a further aspect of the invention, because said exchanging device and/or said apparatus comprise cartridge drive means for advancing both used and new cartridge from and in said receptable opening.

Another embodiment of the after loader apparatus according to the invention is characterized in that, said exchanging device comprises means for moving each of said two compartments within said device to a position adjacent to said receptable opening. In an alternative embodiment, said after loader apparatus comprises means for moving said receptable opening to a position adjacent to one of said two compartments.

Furthermore said transport means can be present in each after loader cartridge. This significantly reduces the construction of the after loader apparatus, whilst with this embodiment of the after loader cartridge the after loader apparatus no longer requires specific means for connecting the transport means present in the after loader apparatus with each separate cartridge.

The invention also relates to a device for exchanging an after loader cartridge in an after loader apparatus for treatment of tumours in an animal body, which cartridge is mounted in a receptable opening present in the housing of said irradiation apparatus and containing at least one radiation source and a transport wire.

For a safe and automatic replacement of a used cartridge with a new cartridge, such in order to prevent possible handling errors of technical personnel, the exchanging device is according to the invention characterized in that said device comprises a radiation shielded housing with a first empty compartment for, in use, receiving said used after loader cartridge mounted in said receptable opening and a second compartment containing a further cartridge with a new radiation source to be inserted in the, now empty, receptable opening.

The cartridges can be constructed in a cheaper, simplified manner with reduced dimensions and weight, whilst maintaining the necessary radiation shielding even when used for HDR or PDR sources. It will be apparent that the handling of such cartridges by technical personnel is improved. Moreover a permanent protection against radiation of the personnel is assured.

More specifically the exchanging device comprises in one embodiment connection means for connecting the housing of the device to the housing of the after loader apparatus, such that said compartments are adjacent to said receptable opening. Thus, the exchange of the cartridges is fully shielded against possible interruption by technical personnel, furthermore it provides a completely shielded construction against possible exposure due to leakage of radiation.

With another specific embodiment cartridge drive means a present for advancing both the used and the new cartridge from and in said receptable opening. In particularly compartment drive means are present for moving each of said two compartments within the device to a position adjacent to said receptable opening.

Further scope of the applicability of the present invention will become apparent from the detailed description given hereinafter. However, it should be understood that the detailed description and specific examples, while indicating preferred embodiment's of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE DRAWINGS

Figure 1:
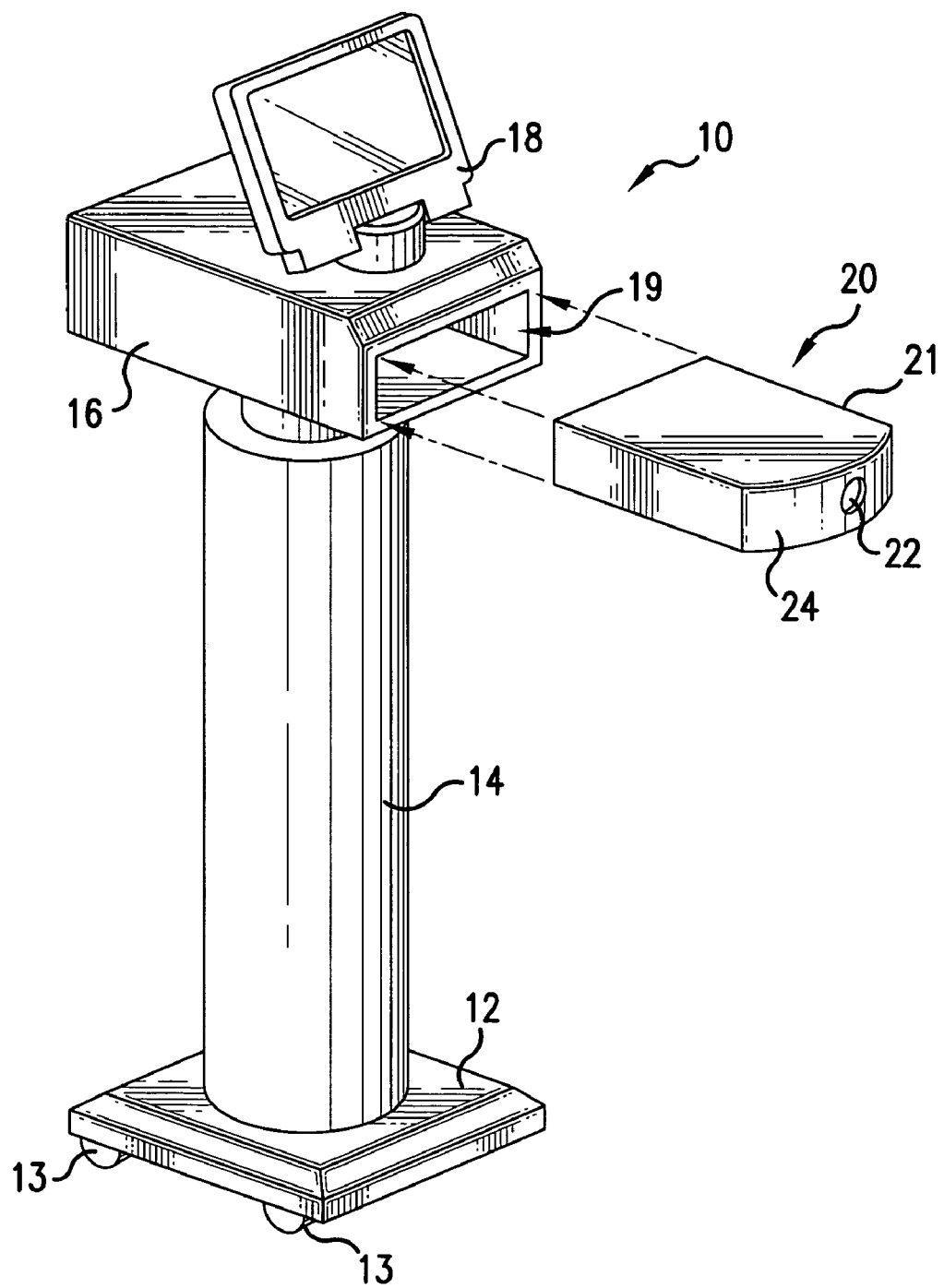
FIG. 1 an after loader apparatus according to the state of the art.

FIG. 1 illustrates an embodiment of an after loader apparatus according to the state of the art, as for example disclosed in U.S. Pat. No. 6,048,300, which is designated generally by reference numeral 10. The after loader apparatus 10 comprises a base 12, which is preferably placed on wheels 13, a pedestal 14 and a head 16 which is vertically adjustable with respect to the pedestal 14 by means of an adjustment mechanism (not shown). An appropriate handle (not shown) may be mounted to the base or pedestal 14 for use in positioning the apparatus 10 in a desired location.

The head 16 may support a video monitor screen 18, such as an LCD touch screen display or the like. He presence and use of such screen for programming and controlling purposes may be optional. Especially after loader devices equipped with HDR or PDR sources are not provided with a screen mounted on the head, as programming and controlling such after loader devices is performed in a control room at a different location properly shielded from the treatment room, in order to remote control the after loader.

The front or forward end of the head 16 is provided with a receptable opening 19 for removably receiving a replaceable cartridge or cassette 20.

The cartridge 20 comprises a housing 21 with a source wire opening 22 in the front wall 24 thereof. The cartridge 20 contains two elongate wires, namely, an active source wire and a dummy test wire, each stored on a respective storage/drive drum, a radiation shield or safe and necessary sensing, monitoring and software components of the system. Optionally, the cartridge 20 can be provided with suitable drive or transport means for advancing the source wire and/or the test wire through the source wire opening 22 through a guide tube (not shown) connected to said source wire opening towards a tumour in an animal body.

Replaceable cartridges 20 are preferably provided by the after loader manufacturer or its distributor with all components loaded and tested including the radiation source connected to said source wire, so that when a cartridge is inserted into the receptacle opening 19 and mechanically and electrically engaged with the mating system connections in the head 16, the after loader apparatus is ready for use in a medical procedure.

The medical procedure initiates with placing the after loader apparatus together with a cartridge 20 inserted into the receptable opening 19 near the patient to be treated. Prior to the radiation treatment one or more guide tubes (catheters, needles, or other closed pathways) are positioned/inserted into the patient's body in or near a cancerous tumour to be treated. Said guide tubes are connected to the source wire opening 22 (or a multiple of source wire openings) and source wire drive means (not shown) present in the cartridge 20 or in the head 16 are activated for advancing the source wire together with the radiation source through an internal guidance path within the cartridge 20, through the source wire opening 22 and through the guide tube (not shown) connected to this source wire opening 22 towards or near the tumour to be treated. Subsequently the radiation source delivers a therapeutic, predetermined dose of radiation to the tumour during specific pre-planned periods of time.

The radiation is emitted towards the tumour under the principals of radioactive decay of radioactive material. After the radiation treatment the source wire drive means retract the source wire together with the radiation source within the cartridge 20. Subsequently the source wire can be advanced through another guide tube towards a different location near or in the tumour to be treated. Thus dependent on the necessary pre-planned treatment it is possible to perform multiple treatment sessions with the same radioactive source on multiple, different treatment locations within a patient's body.

As the radiation emitting source presently used are radioactive sources, which continuously emits gamma radiation the cartridges 20 as presently used have a radiation shielded housing 21 in order to avoid unnecessary exposure of radiation towards the environment, in particularly to medical personal and the patient.

However due to the radioactive decay of radioactive material the radioactive sources presently used need to be replaced in regular intervals and hence the cartridge 20 containing a source wire with an used radioactive source within has to be replaced by a new cartridge 20' having a new radioactive source for future treatment purposes.

However an used source, which has to be replaced by a new source still emits gamma radiation and therefore constitutes a high health risk for the environment, especially when a HDR or PDR source is used. Therefore the replacement of the used radioactive source with a new radioactive source may only performed under well controlled conditions or circumstances and may only performed by high qualified personal. However in some radioactive treatment applications so called high doses radioactive sources (HDR sources) are used, which sources still emits a dangerous amount of radiation at the time that said source needs to be replaced.

The present invention provides a solution for exchanging an cartridge of an after loader apparatus containing an used radioactive source with another cartridge containing a new radioactive source.

FIGS. 2A–2D disclose an embodiment in schematic views of an device for exchanging an after loader cartridge in an after loader apparatus, which device is depicted by reference number 30. Corresponding parts of the after loader apparatus of FIG. 1 are in the FIGS. 2A–2D depicted by the same reference numerals.

The device for exchanging an after loader cartridge in an after loader apparatus according to the invention comprises a base on which a radiation shielded housing 32 is mounted. The radiation shielded housing 32 comprises a first compartment 34, which first compartment 34 in first step can be brought in alignment with the receptable opening 19 of the after loader apparatus 10 containing the used cartridge 20 to be replaced.

In an embodiment the housing 32 of the cartridge exchange device according to the invention can be connected with the housing 16 of the after loader apparatus 10 by suitable connection means (not shown) near point A, were the first compartment 36 is brought in alignment with the receptable opening 19 of the apparatus 10. In compartment 36 of the housing 32 of the exchanging device 30 are cartridge drive means present, comprising an connection block 33 which can be connected to the cartridge 20 to be exchanged, which cartridge 20 is present in the receptable opening 19 of the after loader apparatus 10.

The connection block 33 is preferably made of a suitable radiation shielded material such as tungsten, lead or another suitable material. By means of controllable drive means which are part of the cartridge drive means the connection block 33 is moved in the direction shown in FIG. 2B thereby advancing the used cartridge 20 from its receptable opening 19 of the after loader apparatus 10 into the first compartment 36 of the housing 32.

Due to the fact that both the exchanging device 30 and the after loader apparatus 10 are interconnected with each other near the point A were both the first compartment 36 and the receptable opening are brought in alignment no risk of any radiation emitting towards the environment can occur, as the used cartridge 20 is shielded by the radiation shielded housing 16 of the after loader apparatus 10, the radiation shielded housing 32 of the exchanging device 30 and the connection block 33.

In a subsequent step the housing 16 of the after loader apparatus 10 is disconnected from the housing 32 near the first alignment point A and displaced in vertical direction along the pedestal 14 by means of the adjustment mechanism (not shown) as described above on the reference with FIG. 1.

Figure 2A:
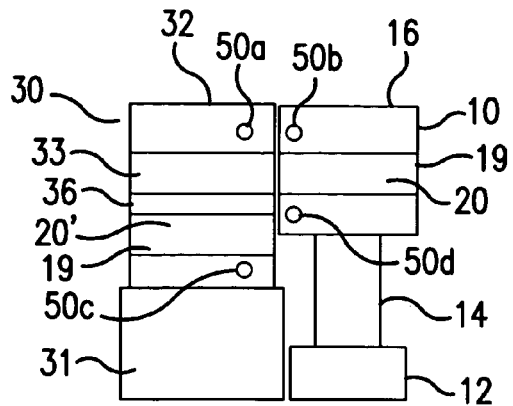
FIGS. 2a–2d schematic views of an embodiment of the cartridge exchange means for use with an after loader cartridge of FIG. 1.
Figure 2B:
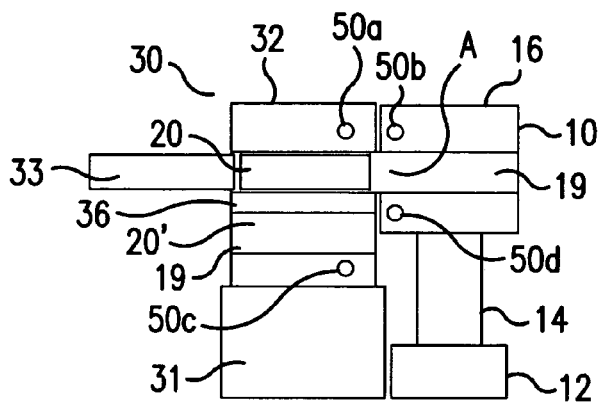
Figure 2C:
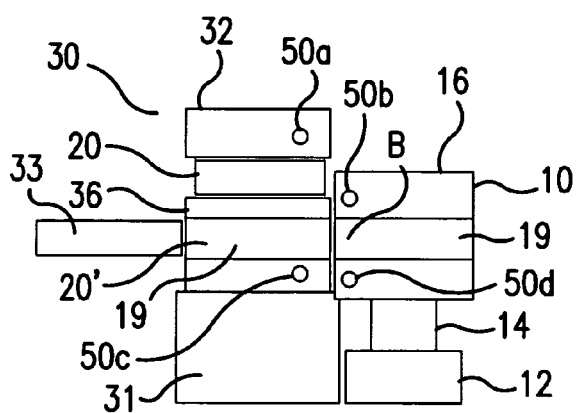

As shown in FIG. 2C the head 16 has been displaced in vertical direction along the pedestal 14 and has been brought in alignment near point B with a second compartment, depicted with reference number 35, wherein a new cartridge 20' containing a new radioactive source is present. In a similar manner as disclosed in FIGS. 2A and 2B connection means are present on the housing 32 and on the head 16 to connect the after loader apparatus 10 with the exchanging device 30 near the alignment point B, thus ensuring a proper radiation shielding and protection for the environment.

Moreover the connection block 33, as being a part of the cartridge drive means, has been brought in alignment with the second compartment 35 at the other side of the exchange device 30 near point C as depicted in FIG. 2C.

The latter is established for example by means of suitable guidance and connecting means present on the outside of the housing 32 for guiding and displacing the connection block 33 from its position as depicted in FIG. 2B towards position C as depicted in FIG. 2C. By advancing the connection block 33 by means of the cartridge drive means into the housing 32 of the exchanging device 30 the new cartridge 20' is pushed into the now empty receptable opening 19 of the after loader apparatus 10.

Figure 2D:
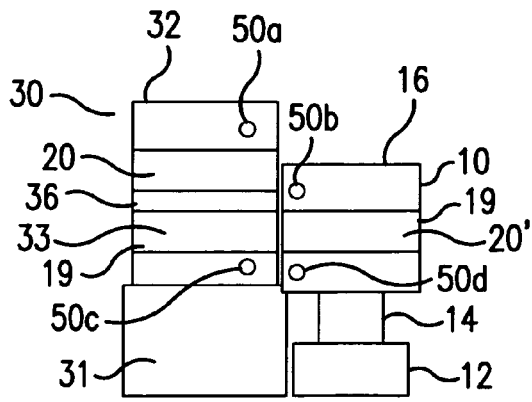

The situation wherein the cartridge 20' containing the new radioactive source is inserted into the receptable opening 19 is depicted in FIG. 2D. Connection block 33 of the cartridge drive means is now present in the second compartment 35.

Between the first compartment 34 and the second compartment 35 a shielding plate 36 is present for providing an additional radiation shielding against high energy gamma radiation emitted by the new high dose rate radioactive source present in the cartridge 20'. Thus the additional radioactive shielding plate 35 provides an additional shielding against gamma radiation for the environment and especially during the insertion of the cartridge 20' from the compartment 35 into the receptable opening 19.

Once the new cartridge 20' has been inserted into the after loader apparatus 10 as depicted in FIG. 2D, the after loader apparatus 10 and the exchange device 30 are disconnected from each other and the after loader apparatus 10 is ready for the application of radioactive treatments, as described above.

Although in one embodiment the exchanging device 30 according to the invention is provided with suitable cartridge drive means for retracting the cartridge 20 with the used radioactive source from the receptable opening 19 into the first compartment 34 in a controlled manner, which cartridge drive means moreover displace the connection element 33 from its position depicted in FIG. 2B towards his position depicted in FIG. 2C, it is noted that in another embodiment the replacement of the used cartridge 20 with a new cartridge 20' can also be performed by hand, as long as the connection element 33 is connected in its alignment point A with the used cartridge 20, in order to enable a smooth and easy removal of the used cartridge 20 from the receptable opening 19 of the after loader apparatus 10.

Furthermore disclose FIGS. 2A–2D one or more pairs of sensor means 50a–50b and 50c–50d, which sensors are provided in the housing 16 of the after loader device 10 and the housing 32 of the exchanging device 30. The sensor pairs serve to obtain a proper and correct alignment between the first and second compartments 34–35 with the receptable opening 19. The correct alignment is performed by displacing the housing 16 of the after loader in vertical direction along the pedestal 14 by suitable displacement means (not shown). Once at least one of the sensors 50b senses the corresponding sensor 50a a signal is delivered to the control means of the after loader device, which abrupt the displacement of the housing 16 by controlling the displacement means.

Now both the first compartment 34 and the receptable opening 19 are brought in alignment and the connection means near point A present on both housings 16 and 32 (see FIG. 2A) can interconnect with each other.

Once the used cartridge 20 has been moved from the receptable opening 19 into the first compartment 34 (see FIG. 2B), the connection means are disconnected and the housing 16 is displaced in vertical direction along the pedestal 14. At least one of the sensors 50d present on the housing 16 senses the presence of a corresponding sensor 50c present on the housing 32 of the exchanging device 30 in order to obtain a correct alignment between the empty receptable opening 19 and the second compartment containing the new cartridge 20' (Point B in FIG. 2C).

In a similar way the sensor 50d delivers a control signal to the control means of the after loader device once the sensor 50c is sensed in order to stop the movement of the housing 16 along the pedestal 14 by means of the displacement means (FIG. 2D).

Although in FIGS. 2A–2D only one of each sensor 50a–50d is shown, a more accurate alignment can be obtained by placing two or more sensors 50b, 50d around the receptable opening 19 in the housing 16, which plurality of sensors 50b–50d cooperate with a corresponding plurality of sensors 50a–50c present in the housing 32 of the exchanging device.

Although the sensing of sensors 50a and 50c by the sensors 50b respectively 50d primarily is used for interrupting the movement in vertical direction of the housing 16 of the after loader device, the sensors 50a–50d can also be used to deliver control signals to the control means of both the after loader device and the exchanging device for controlling the cartridge drive means for the automatic displacement of the used cartridge 20 from the receptable opening 19 towards the first compartment 34 and the displacement of the new cartridge 20 from the second compartment 35 towards the receptable opening 19

Figure 3A:
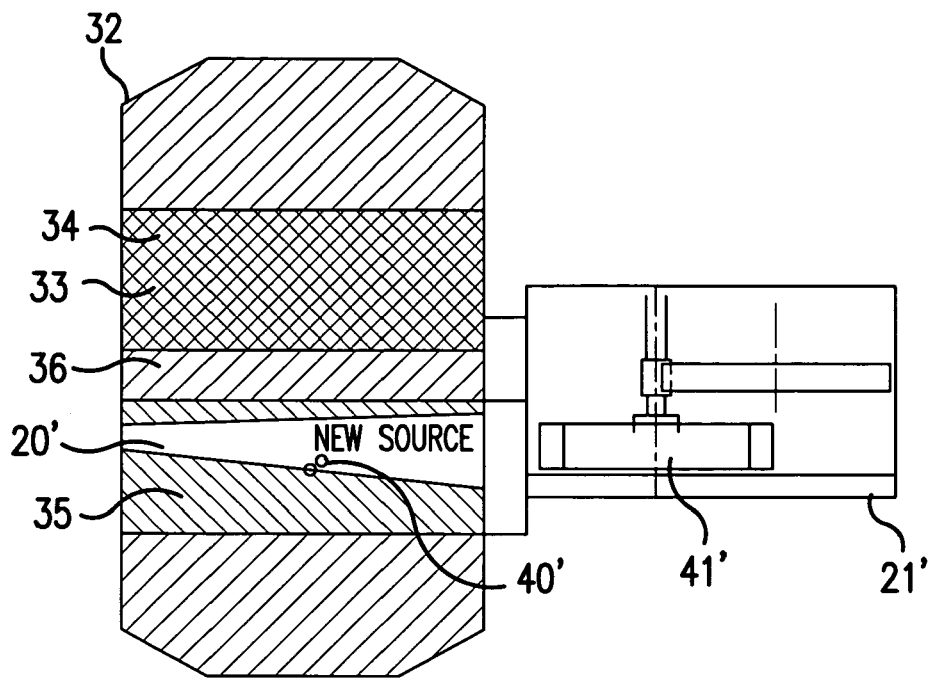
FIGS. 3a–3c views in more detail of the cartridge exchange means of the invention.
Figure 3B:
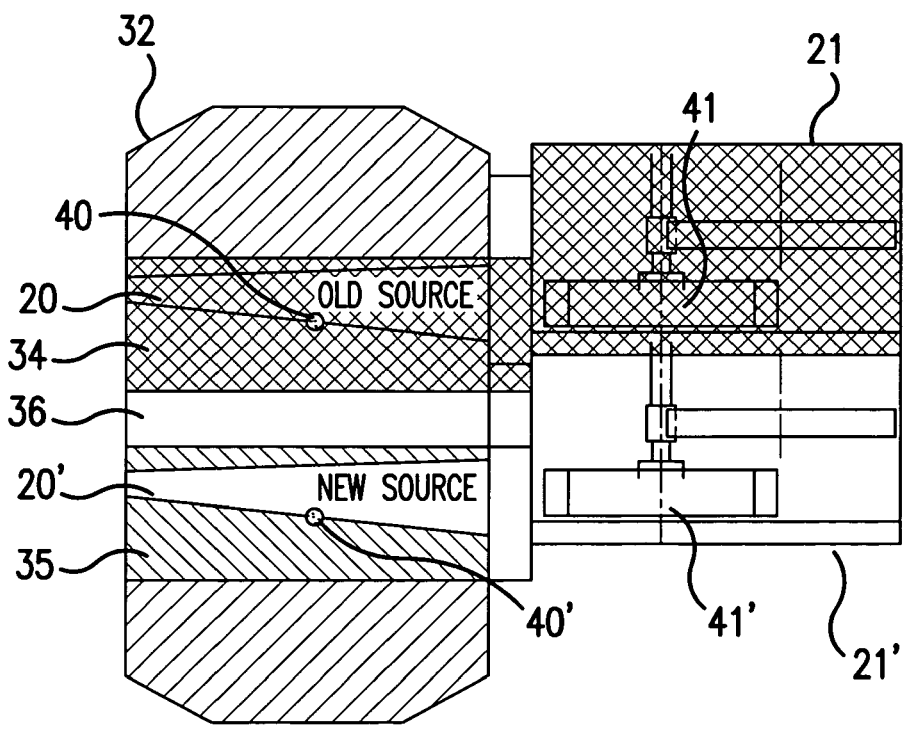
Figure 3C:
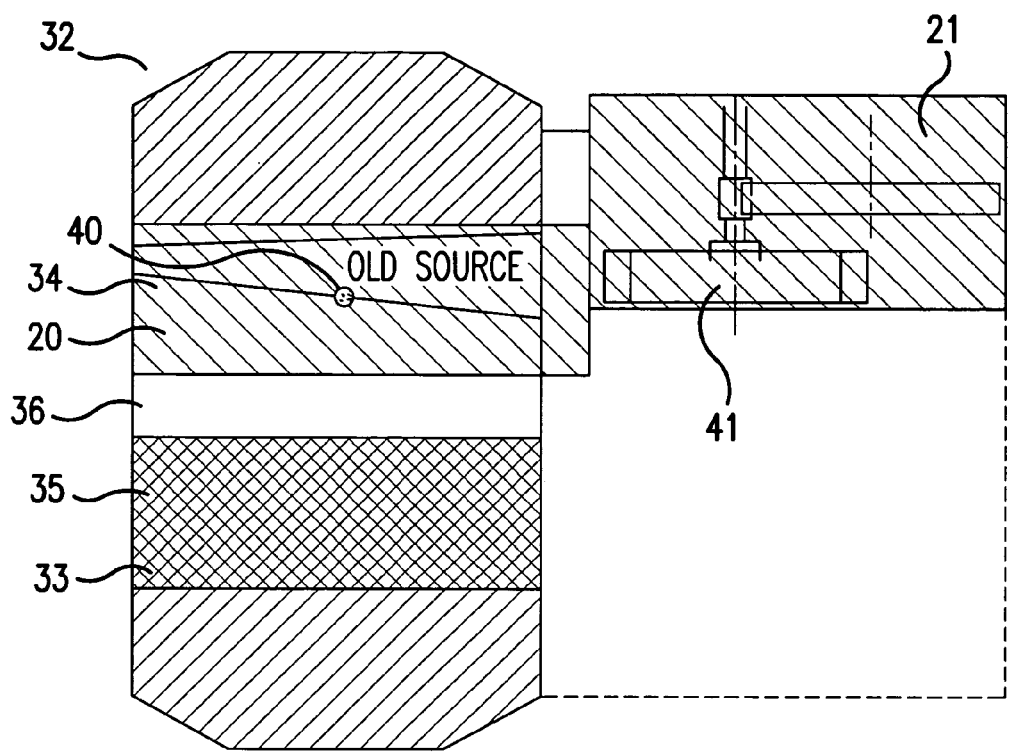

FIGS. 3A–3C show in more detail the exchanging device according to the invention. FIG. 3A correspond with the FIG. 2A with a cartridge 20' containing a new radiation source 40', which cartridge is contained in second compartment 35 present in the housing 32 of the exchanging device according to the invention. Moreover a connection block 33 as being a part of the cartridge drive means is present in the first compartment 34.

FIG. 3B discloses the situation depicted in FIGS. 2B and 2C, wherein the old cartridge 20 containing the used radiation source 40 is displaced from the receptable opening 19 of the after loader apparatus 10 (not shown) and inserted into the first compartment 34 of the radiation shielded housing 32. FIG. 3C discloses the situation depicted in FIG. 2D, wherein the new cartridge 20' has been displaced by the connection element 33 into the receptable opening 19 of the after loader apparatus 10 (not shown). The exchanging device 30, only containing the used cartridge 20 into the first compartment 34 can now be transported towards the manufacturer of the radiation source in order to perform further handling operations on the used cartridge 20 and its used radiation source 40.

Subsequently the exchanging device 30 can be prepared and provided with a new radiation source contained in a new cartridge for an future exchanging procedure.

As shown in FIGS. 3A–3C the cartridges 20 and 20' respectively may comprise an additional housing 21 and 21' respectively, wherein suitable source wire and source drive means 41 and 41' are present. Preferably said additional housings 21 and 21' are non- or less-radiation shielded than the housing 20 and 20', as they do not contain the radioactive source nor function as a long-distance radiation source transport container for stand alone storage and transportation of the used source.

Thus an after loader cartridge having a significant simplified construction with reduced dimensions and weight is obtained.

Figure 4A:
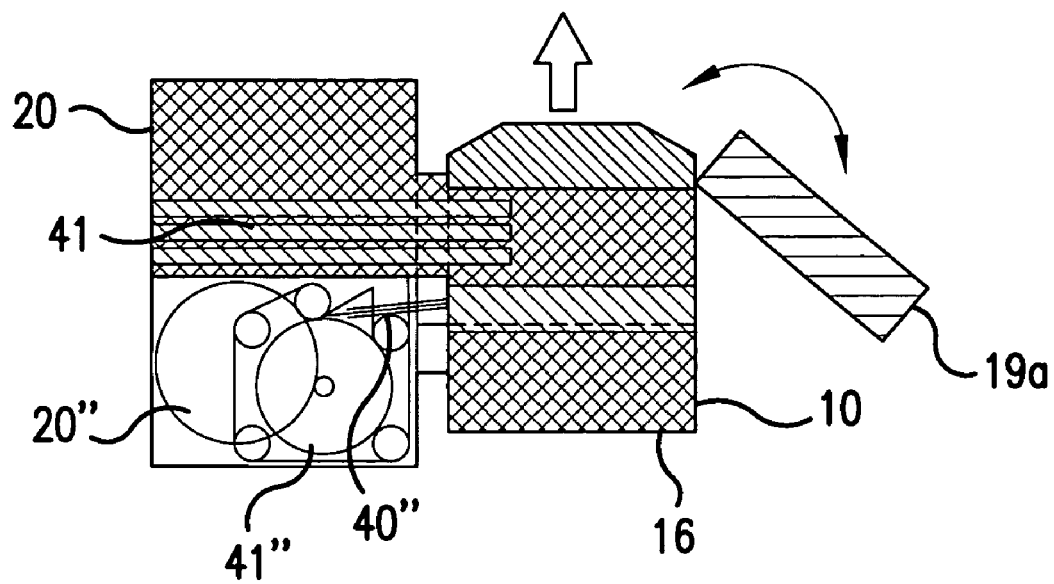
FIGS. 4a–4b a top view and a side view of an after loader cartridge with a cartridge.
Figure 4B:
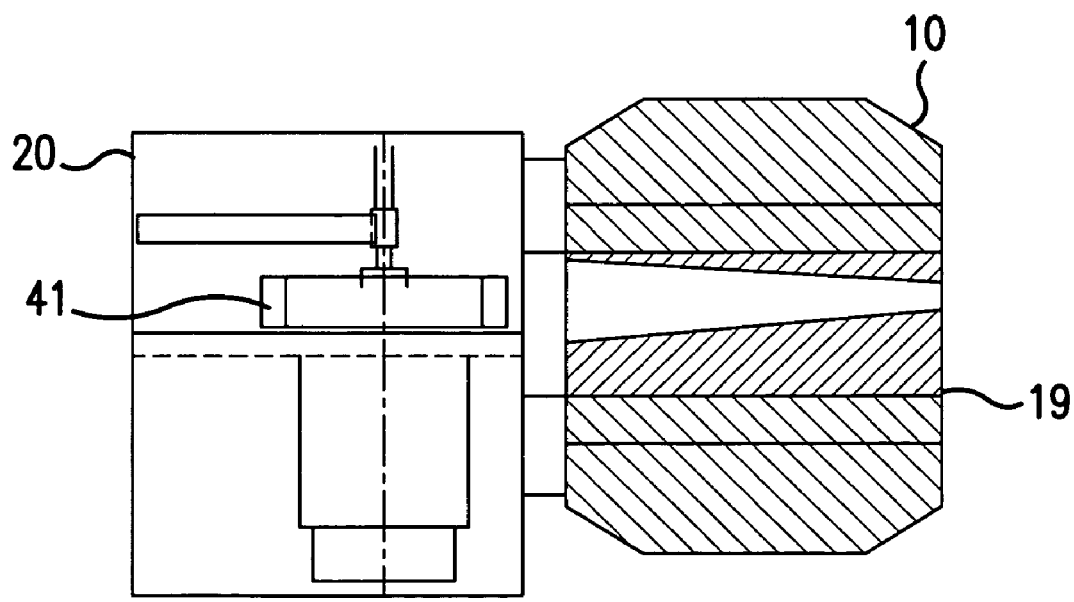

FIGS. 4A–4B disclose an after loader device 10 according to the invention, wherein the radiation shielding part of housing 16 is depicted in dashed lines. The receptable opening 19 can be closed by means of part 19a of the shielding. The cartridge 20 contains one elongate wire, namely, an active source wire with a radioactive source 40 (not shown), whilst a dummy test wire 40" is contained stored inside the after loader device. Each wire 40–40" is stored on a respective storage/drive drum 41a–41a", each being mounted inside the cartridge 20 and the housing 16 of the after loader device, respectively. The cartridge 20 is provided with suitable drive or transport means 41 for advancing the source wire 40, whilst the after loader device comprises suitable drive or transport means 41" for advancing the test "dummy" wire 40". During use both transport means 41–41" advances the source wire 40 or the test wire 40" respectively through the guidance path 22a present in the radiation shielded part 20a of the cartridge 20, through the source Wire opening 22 (see also FIG. 1), through a guide tube (not shown) connected to said source wire opening towards a tumour in an animal body.

The guidance path 22a is a spiral line of groove present in the cone shaped surface as shown in FIG. 4B in order to ensure a proper guidance of the wire through the cartridge towards the opening 22.

The dummy wire 40" is contained in a part 20" of the housing 16 of the after loading device, which part 20" does not be radiation shielded as the dummy wire does not contain a radioactive wire. In order to replace or exchange the cartridge 20 the dummy wire is retracted by the wire drive means 41" prior to the removal of the cartridge 20 through the receptable opening 19.

Figure 5A:
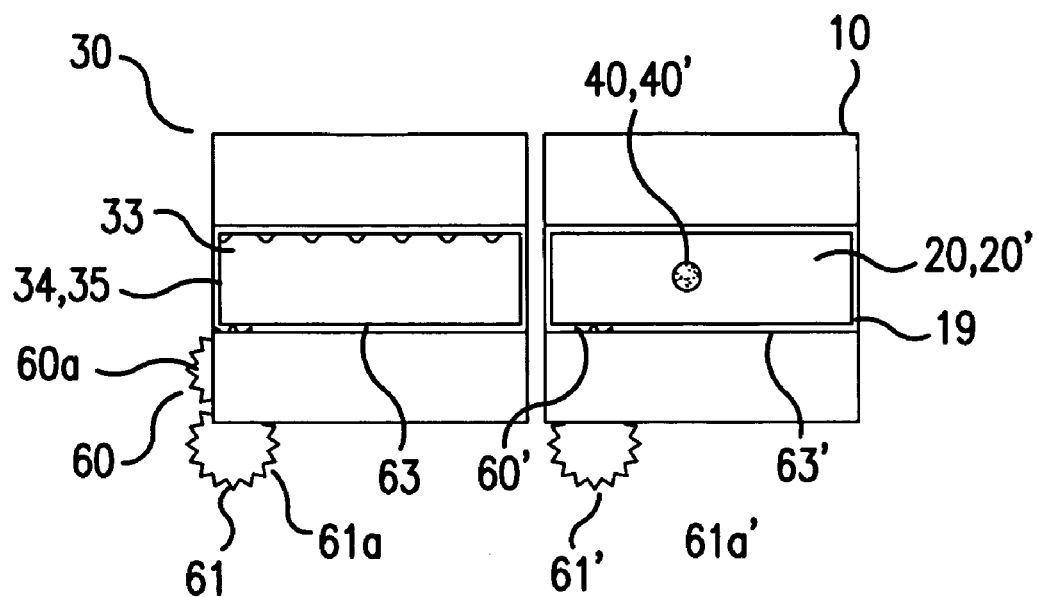
FIGS. 5a–5b another embodiment of specific cartridge drive means for displacing the used and new cartridges according to the invention.
Figure 5B:
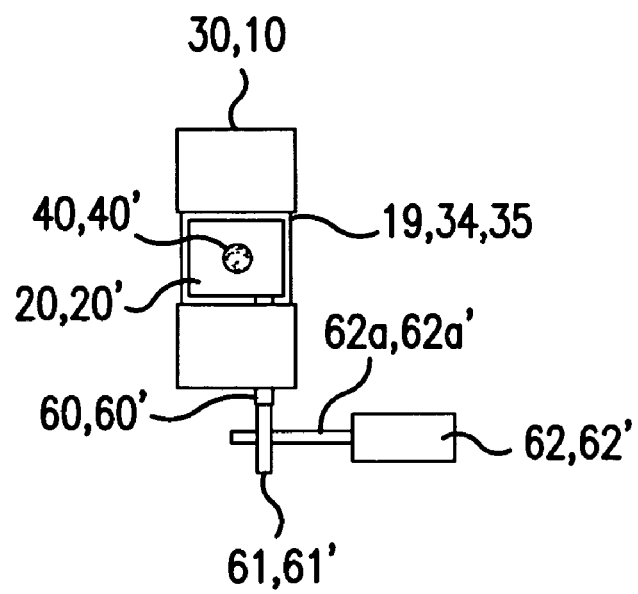

FIGS. 5A–5B discloses a specific embodiment of the cartridge drive means according to the invention present in both the after loader device and the exchanging device for displacing both the used and new cartridges 20 and 20' between the receptable opening 19 and both compartments 34 and 35.

The cartridge drive means comprise at least one drivable wheel 60 for advancing both used and new cartridge 20 and 20', wherein the advancement can be performed by means of friction. The drivable wheel can thereby be brought into contact with the used or new cartridge 20 respectively 20'.

Another preferred embodiment is however disclosed in FIGS. 5A–5B, wherein said at least one drivable wheel of the cartridge drive means of the after loader device 10 is a toothed wheel 60' with teeth 60a', which teeth 60a' cooperates with a corresponding toothing 63a' of another wheel 63' present in the housing of said used cartridge 20. Said wheel 60' is driven by said toothed wheel 61', which is mounted on the drivable axis 62a of an electromotor 62'.

In a similar way contain the cartridge drive means of the exchanging device 30 at least one drivable wheel 60 with teeth 60a, which teeth 60a cooperates with the corresponding toothing 63' present in the housing of said used cartridge 20 or with the corresponding toothing 63' present in the housing of the new cartridge 20' or with a corresponding toothing 63 present in said element 33. Said wheel 60 is driven by another toothed wheel 61, which is mounted on the drivable axis 62a of an electromotor 62 present in the exchanging device 30.

The control of the both motors 62–62' is performed by the control means of either the after loader device 10 or the exchanging device 30 and is based for example on the signals delivered by the sensors 50a–50d shown and described above in combination with FIGS. 2A–2D. In combination with FIG. 2A once the sensor 50b senses sensor 50a thereby assuring a proper alignment of the receptable opening 19 with the empty first compartment 34 the cartridge drive means of the after loader device displace the used cartridge 20 under the influence of the interaction between the toothed wheel 60' with the toothing 63' present on the used cartridge 20.

The displacement of the used cartridge 20 may be taken over by the cartridge drive means of the exchanging device (the interaction between the toothing 63' of the used cartridge 20 and the toothed wheel 60 present near the first compartment).

In a similar way the cartridge drive means present near the second compartment of the exchanging device can displace a new cartridge 20' from the second compartment towards the empty receptable opening as shown in FIGS. 2C–2D, where the displacement of the new cartridge 20' may be taken over by the toothed wheel 60' of the cartridge drive means of the after loader device based on signals delivered by the sensors 50c–50d.

However the displacement of each cartridge 20–20' can be performed solely by the cartridge drive means of the after loader device (for displacing the used cartridge 20 from the opening 19 towards the first compartment) or solely by the cartridge drive means present near the second compartment (for displacing the new cartridge 20' from the second compartment towards the receptable opening 19).

Furthermore according to another aspect of the invention both used and new cartridge may include means for identifying the radiation source contained in it, wherein said identification means can comprise an electronic (integrated) circuitry containing at least a memory, wherein said identification parameters can be read and stored.

Said identification parameters may include information concerning the radiation source, such as initial radioactive activity, date of calibration, radioactive half-time, serial numbers, as well as information concerning the transport means, the type of transport cable, and characteristics of the shielding.

More especially the after loader device comprises means, which cooperate with the identification means for a proper recognition, handling and operation of both the used and new cartridge, for example when performing the intended radioactive therapy treatment. Said means may read in a contact less way the essential identification parameters from the memory means in order to properly preset and control the after loader device during therapy treatments.

Figure 6:
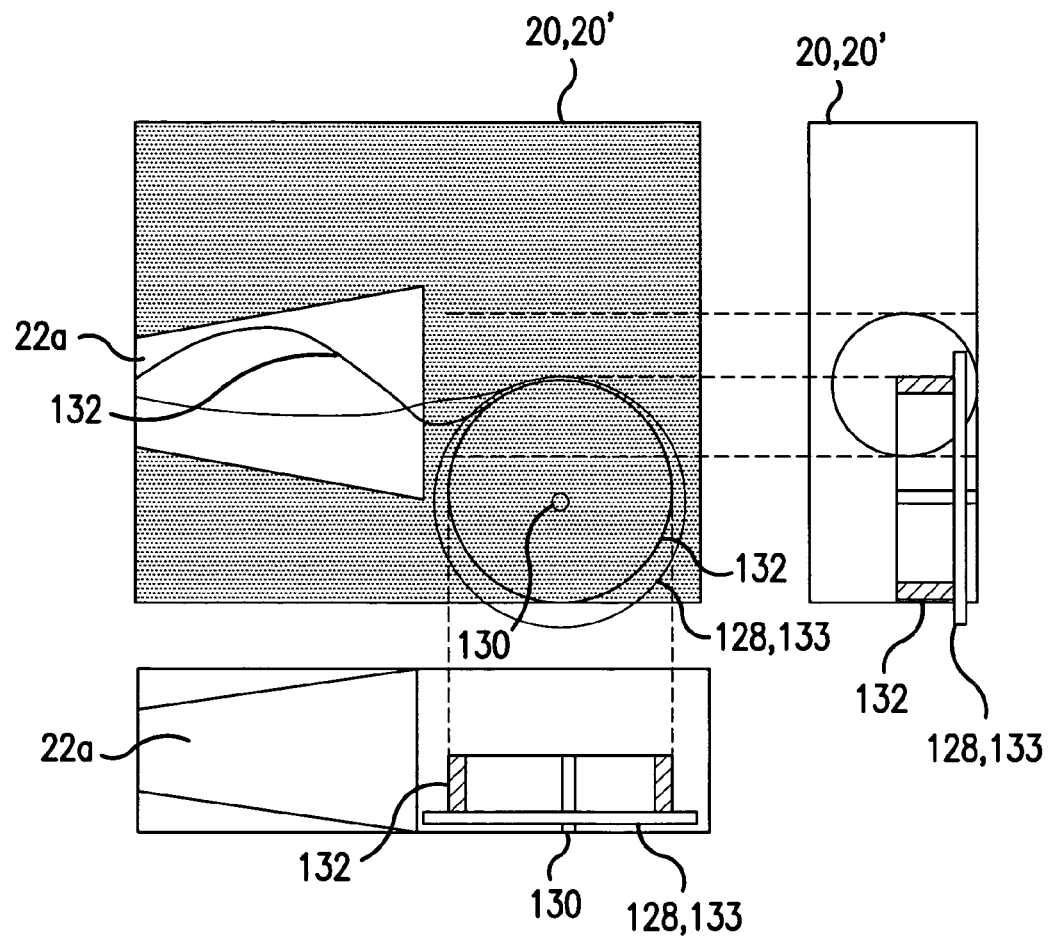
FIGS. 6, 7a–7c another embodiment of a cartridge for use in the after loader device according the invention.

In FIG. 6 another embodiment is disclosed of a cartridge for use in the after loader device and exchanging device according to the invention. At present the transport or drive means for advancing the source wire together with the radioactive source are incorporated inside the housing 16 of the after loader device. Such wire transport/drive means are for example disclosed in the European patent application no. 1070519 in the name of Nucletron B.V., the application of this application.

Figure 7A:
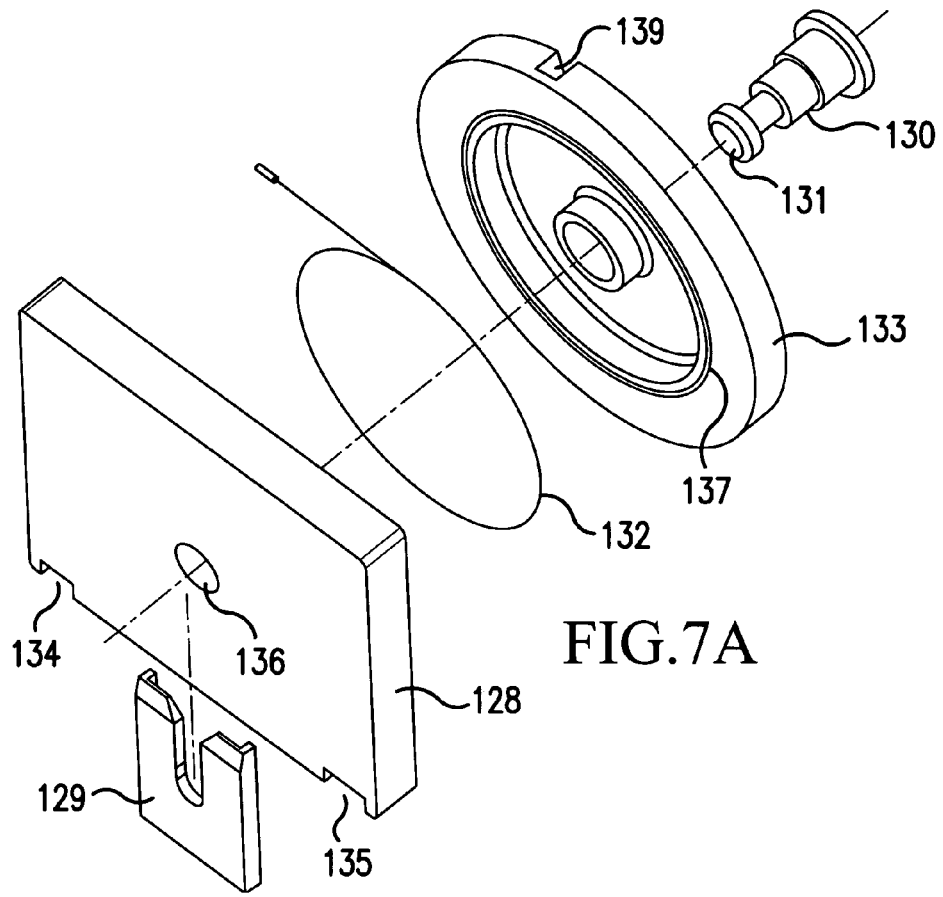
Figure 7B:
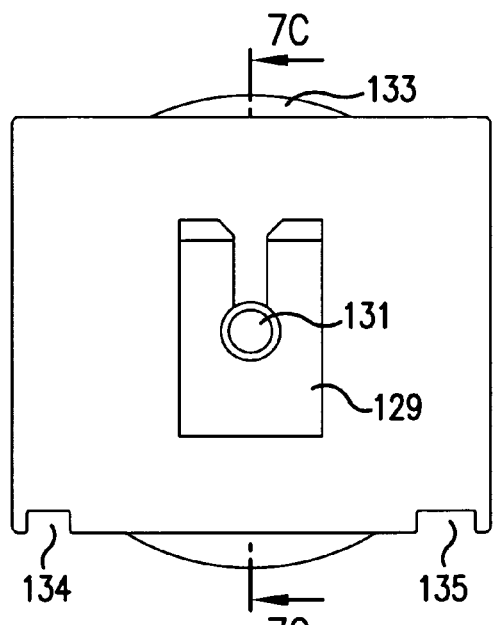
Figure 7C:
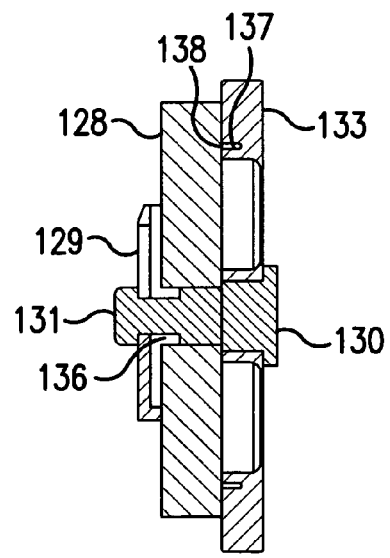

The disclosure of the transport/drive means for the wire is herewith incorporated by reference. As shown in FIGS. 7A–7C drive means for the wire 132 comprise a support plate or housing 128, a fixing plate 129, a multi-diameter shaft 130 with a top 131, a wire 132 and a wire storage wheel 133. The support plate 128 is provided with support notches 134 and 135 and a central opening 136. Support plate 128 further is provided with a straight groove 138. The height and width of groove 138 are essentially the same as the diameter of the wire 132. Multi-diameter shaft 130 comprises a top 131 of a diameter at most as large as the diameter of opening 136 in support plate 128.

Top 131 is followed by a first part of a first diameter that is smaller than the diameter of the top 131, by a second part of a diameter that is substantially equal to the diameter of the opening 136, by a third part of a diameter that is larger than the diameter of the opening 136 and a fourth part with a still larger diameter.

Wire storage wheel or drum 133 comprises a groove 137 having a width being is equal to the diameter of the wire 132. The depth of the groove 137 is equal to several diameters of the wire 132. The radius of the groove 137 is equal to the distance from the centre of the opening 136 to the groove 138. One end of the wire is fixed in the groove 137. The wire 132 is contained in the groove 137 except for its other end. The other end of wire 132 runs from groove 137 into groove 138. Wheel 133 is provided with two, in this exemplary embodiment diametrically opposed, notches, one of which is visible as 139. Wheel 133 can be driven by a motor (not shown) via shaft 130.

The drive means are assembled from the various parts as shown in FIG. 7A and are mounted inside the after loader device according to the state of the art. In the previous described patent application in order to reduce weight the drive means are at present manufactured from plastic.

In order to simplify the exchange of the cartridge 20 the transport/drive means for the wire are embedded inside the housing 16 of the cartridge 20 as shown in FIG. 6. Because of radiation protection reasons, the parts are made from a metal and more in particularly from the same metal of the radiation shielding of the housing 16 of cartridge 20. As the drive means moreover have certain dimensions and thus require/occupy space inside the cartridge 20, the wire drive means are according to the invention at least part of the radiation shielding of the housing 16 of cartridge 20. More in particularly the support housing 128 is made of the same material of the radiation shielding and forms an (integral) part of said shielding.

More in particular the wire transport means are made from tungsten, a metal with a suitable compromise between weight and effective radiation shielding.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A device for exchanging an after loader cartridge in an after loader apparatus for treatment of tumours in an animal body, which cartridge is mounted in a receptable opening present in the housing of said after loader apparatus and containing at least one radiation source and a transport wire, wherein said device comprises a radiation shielded housing arranged to brought in an interacting manner with the housing of said after loader apparatus, said radiation shielded housing being provided with a first empty compartment for, in use, receiving said used after loader cartridge mounted in said receptable opening and a second compartment for containing a further cartridge with a new radiation source to be inserted in the, now empty, receptable opening.

2. The exchanging device according to claim 1, wherein said device comprises connection means for connecting the housing of the device to the housing of the after loader apparatus, such that said compartments are adjacent to said receptable opening.

3. The exchanging device according to claim 2, wherein said connection means are arranged for cooperating with corresponding connection means present on the housing of the after loader apparatus for connecting said exchanging device to the after loader apparatus.

4. The exchanging device according to claim 2, wherein both the connection means comprise means for aligning the exchanging device with the receptable opening.

5. The exchanging device according to claim 4, wherein said aligning means comprise alignment sensors present on at least one of the housing of the exchanging device and the housing of the after loader apparatus.

6. The exchanging device according to claim 1, wherein cartridge drive means are present for advancing both used and new cartridge from and in said receptable opening.

7. The exchanging device according to claim 6, wherein said cartridge drive means comprise a connection element to be brought in contact with both used or new cartridge.

8. The exchanging device according to claim 6, wherein said cartridge drive means comprise at least one drivable wheel for advancing both used and new cartridge.

9. The exchanging device according to claim 8, wherein said at least one drivable wheel advances said used and new cartridge by friction.

10. The exchanging device according to claim 9, wherein said at least one drivable wheel is a toothed wheel, which cooperates with a corresponding toothing present on said connection element or said used and new cartridge respectively.

11. The exchanging device according to claim 1, wherein compartment drive means are present for moving each of said two compartments within the device to a position adjacent to said receptable opening.

12. The exchanging device according to claim 1, wherein the wall within the housing separating both of the compartments is made of a radiation shielded material.

13. The exchanging device according to claim 1, wherein the device comprises means, which cooperate with identification means present in both used and new cartridge and intended for identifying the radiation source contained therein, said cooperation means being arranged for a proper recognition, handling and operation of both the used and new cartridge.

14. An exchangeable radiation shielded after loader cartridge for use in an exchanging device as described in claim 1, comprising at least one exchangeable radiation source connected to a first end of a transport cable, which cable is to be connected with its other end to transport means for advancing said transport cable and said radiation source through a guide tube to and from a tumour in said body, wherein for exchanging purposes the cartridge is arranged for corporation with at least one of the cartridge drive means of said exchanging device and said after loader apparatus, wherein said after loader cartridge is provided with a toothing for corporation with a toothed wheel of said cartridge drive means.

15. The apparatus according to claim 14, wherein said apparatus comprises means for moving said receptable opening to a position adjacent to one of said two compartments.

16. The after loader cartridge according to claim 14, wherein said transport means are present in each after loader cartridge.

17. The after loader cartridge according to claim 16, wherein said transport means are part from the radiation shielding of said cartridge.

18. The after loader cartridge according to claim 17, wherein said transport means are made from the same material as the radiation shielding.

19. The after loader cartridge according to claim 14, wherein both used and new cartridge include means for identifying the radiation source contained therein.

20. The after loader cartridge according to claim 19, wherein said identification means comprise an electronic memory, wherein identification parameters are stored.

21. The after loader cartridge according to claim 19, wherein said identification parameters may include information concerning the radiation source, the information being at least one of initial radioactive activity, date of calibration, radioactive half-time, serial numbers, information concerning the transport means, the type of transport cable, and characteristics of the shielding.

22. An after loader apparatus for treatment of tumours in an animal body, said apparatus comprising a housing with at least one exchangeable radiation source connected to a first end of a transport cable, the cable being connected with its other end to transport means for advancing said transport cable and said radiation source through a guide tube to and from a tumour in said body, where at least the radiation source and the transport cable are mounted in an exchangeable radiation shielded after loader cartridge, the cartridge is placeable in a suitable receptable opening present in said housing, wherein for exchanging said radiation source after use of the after loader apparatus is arranged for corporation with an exchanging device as described in claim 1, further comprising connection means present on the housing of the apparatus, which is cooperatable with corresponding connection means present on said exchanging device for connecting said apparatus to said exchanging device.

23. The apparatus according to claim 22, wherein said connection means are mounted around said receptable opening.

24. The apparatus according to claim 22, wherein the connection means comprise means for aligning the exchanging device with the receptable opening.

25. The apparatus according to claim 24, wherein said aligning means comprise alignment sensors present on the housing of the apparatus.

26. The apparatus according to claim 22, wherein said apparatus comprise cartridge drive means for advancing both used and new cartridge from and in said receptable opening.

27. The apparatus according to claim 26, wherein said cartridge drive means comprise a connection element to be brought in contact with both used and new cartridge.

28. The apparatus according to claim 26, wherein said cartridge drive means comprise at least one drivable wheel for advancing both used and new cartridge.

29. The apparatus according to claim 28, wherein said at least one drivable wheel advances said used and new cartridge by friction.

30. The apparatus according to claim 28, wherein said at least one drivable wheel is a toothed wheel, which cooperates with a corresponding toothing present on said used and new cartridge.

31. An exchangeable radiation shielded after loader cartridge for use in an after loader apparatus as described in claim 22, comprising at least one exchangeable radiation source connected to a first end of a transport cable, which cable is to be connected with its other end to transport means for advancing said transport cable and said radiation source through a guide tube to and from a tumour in said body, wherein for exchanging purposes the cartridge is arranged for corporation with at least one of the cartridge drive means of said exchanging device and said after loader apparatus, wherein said after loader cartridge is provided with a toothing for corporation with a toothed wheel of said cartridge drive means.

32. The after loader cartridge according to claim 31, wherein said transport means are present in each after loader cartridge.

33. The after loader cartridge according to claim 32, wherein said transport means are part from the radiation shielding of said cartridge.

34. The after loader cartridge according to claim 33, wherein said transport means are made from the same material as the radiation shielding.

35. The after loader cartridge according to claim 31, wherein both used and new cartridge include means for identifying the radiation source contained therein.

36. The after loader cartridge according to claim 35, wherein said identification means comprise an electronic memory, wherein identification parameters are stored.

37. The after loader cartridge according to claim 35, wherein said identification parameters may include information concerning the radiation source, the information being at least one of initial radioactive activity, date of calibration, radioactive half-time, serial numbers, information concerning the transport means, the type of transport cable, and characteristics of the shielding.

* * * * *